(12) United States Patent
Owen

(10) Patent No.: US 7,489,810 B2
(45) Date of Patent: *Feb. 10, 2009

(54) METHOD AND SYSTEM FOR LINKING LOCATION INFORMATION BETWEEN SOFTWARE APPLICATIONS FOR VIEWING DIAGNOSTIC MEDICAL IMAGES

(75) Inventor: Frank J. Owen, Elmhurst, IL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 829 days.

This patent is subject to a terminal disclaimer.

(21) Appl. No.: 10/861,339

(22) Filed: Jun. 4, 2004

(65) Prior Publication Data

US 2005/0065423 A1   Mar. 24, 2005

Related U.S. Application Data

(60) Provisional application No. 60/476,756, filed on Jun. 6, 2003.

(51) Int. Cl.
*G06K 9/00* (2006.01)
*A61N 5/00* (2006.01)

(52) U.S. Cl. ...................... 382/128; 600/300
(58) Field of Classification Search .................. 382/128, 382/129–132; 600/300
See application file for complete search history.

(56) References Cited

U.S. PATENT DOCUMENTS

| | | | |
|---|---|---|---|
| 5,531,227 A * | 7/1996 | Schneider | 600/425 |
| 5,954,650 A * | 9/1999 | Saito et al. | 600/425 |
| 6,380,958 B1 * | 4/2002 | Guendel et al. | 715/848 |
| 6,674,449 B1 * | 1/2004 | Banks et al. | 715/740 |
| 7,062,416 B1 * | 6/2006 | Arita et al. | 703/2 |
| 7,103,205 B2 * | 9/2006 | Wang et al. | 382/132 |
| 7,106,891 B2 * | 9/2006 | Wyman et al. | 382/128 |
| 7,346,199 B2 * | 3/2008 | Pfaff | 382/128 |
| 2001/0029334 A1 * | 10/2001 | Graumann et al. | 600/437 |
| 2001/0036302 A1 * | 11/2001 | Miller | 382/128 |
| 2005/0065424 A1 * | 3/2005 | Shah et al. | 600/407 |
| 2006/0165267 A1 * | 7/2006 | Wyman et al. | 382/128 |
| 2007/0003131 A1 * | 1/2007 | Kaufman | 382/154 |
| 2007/0276901 A1 * | 11/2007 | Glinsky et al. | 709/203 |
| 2007/0277115 A1 * | 11/2007 | Glinsky et al. | 715/771 |

\* cited by examiner

*Primary Examiner*—Aaron W Carter
(74) *Attorney, Agent, or Firm*—Andrus, Sceales, Starke & Sawall, LLP

(57) ABSTRACT

A method and system for linking position location information between two-dimensional (2D) and three-dimensional (3D) software applications for viewing diagnostic medical images. The position location information is integrated between 2D and 3D viewing paradigms. This integration provides bidirectional communication between the 2D and 3D viewing paradigm systems. The 3D cursor allows for immediate synchronized navigation through different image sets such as 3D magnetic resonance (MR) images and 2D computed tomography (CT) images while they are being simultaneously viewed on the two different viewing applications.

20 Claims, 6 Drawing Sheets

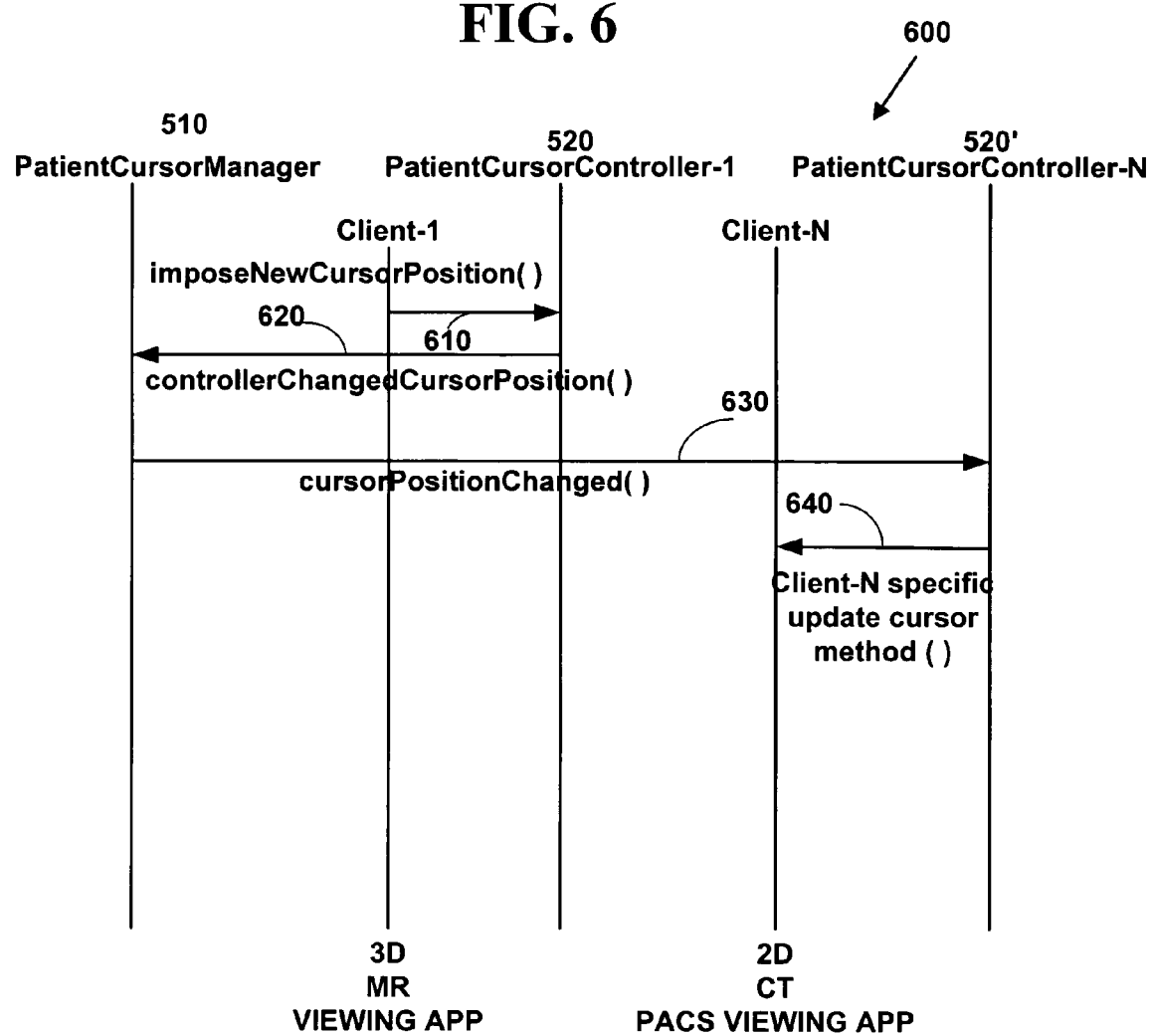

METHOD AND SYSTEM FOR LINKING LOCATION INFORMATION BETWEEN SOFTWARE APPLICATIONS FOR VIEWING DIAGNOSTIC MEDICAL IMAGES

CROSS REFERENCES TO RELATED APPLICATIONS

This patent application claims priority to U.S. Provisional Patent Application, 60/476,756, filed on Jun. 6, 2003, the contents of which are incorporated by reference.

FIELD OF INVENTION

This invention relates to medical diagnostic systems. More specifically, it relates to a method and system for linking location information between software applications for viewing medical diagnostic images.

BACKGROUND OF THE INVENTION

In a modern radiology department, it is often desirable to view three-dimensional (3D) volumetric views and multiplanar reconstructions of patient information in addition to the two-dimensional (2D) raw images acquired during a computed tomography (CT) or magnetic resonance (MR) scan.

As is known in the medical arts, a "CT scan" is a radiographic technique that assimilates multiple X-ray images into a 2D cross-sectional image. An "MR scan" is a technique that uses the influence of a large magnet to polarize hydrogen atoms in the tissues and then monitors the summation of the spinning energies within living cells. It is used to produce 3D images of internal structures of the body, particularly the soft tissues.

These 3D visualizations are typically derived from a base series of 2D images acquired from a method of treatment or "modality" (e.g., CT or MR). Typically only 2D base images are permanently stored on a Picture Archive and Communication System (PACS). The 3D images are generated when needed. As is known in the art, PACS is a computer and network system used by hospitals and clinics for digitized radiologic images and reports.

One problem with viewing 3D images is that the PACS system is capable of displaying original 2D base image sets, but the dynamic generation and display of the derived 3D images are typically relegated to a specialized workstation application tuned for 3D volumetric visualization. This separation of the 2D and 3D images makes it awkward for the radiologist to correlate what (s)he is viewing on the 3D visualization application with the raw 2D image date displayed on the PACS workstation.

Another problem is that there is no easy way to integrate and synchronize spatial context information between separate 2D and 3D viewing applications when viewing the same medical diagnostic image study.

Thus, it is desirable to integrate 2D and 3D image viewing. It is also desirable to integrate these two viewing paradigms synchronizing spatial context information between separate applications when viewing the same diagnostic medical image study.

SUMMARY OF THE INVENTION

In accordance with preferred embodiments of the invention, some of the problems associated viewing different types of medical diagnostic images with are overcome. A method and system for linking position location information between different software applications for viewing diagnostic medical images is presented.

The method and system allow linking of position location information between two-dimensional (2D) and three-dimensional (3D) software applications for viewing diagnostic medical images. The position location information is integrated between 2D and 3D viewing paradigms. This integration provides bidirectional communication between the 2D and 3D viewing paradigm systems. The method and system allows for immediate synchronized navigation through different image sets such as 3D magnetic resonance (MR) images and 2D computed tomography (CT) images while they are being simultaneously viewed on the two different viewing applications.

The foregoing and other features and advantages of preferred embodiments of the invention will be more readily apparent from the following detailed description. The detailed description proceeds with references to the accompanying drawings.

BRIEF DESCRIPTION OF THE DRAWINGS

Preferred embodiments of the invention are described with reference to the following drawings, wherein:

FIG. 6 is a data flow diagram illustrating details of the medical image object architecture.

DETAILED DESCRIPTION OF THE INVENTION

Exemplary Medical Diagnostic Image Viewing System

Figure 1:
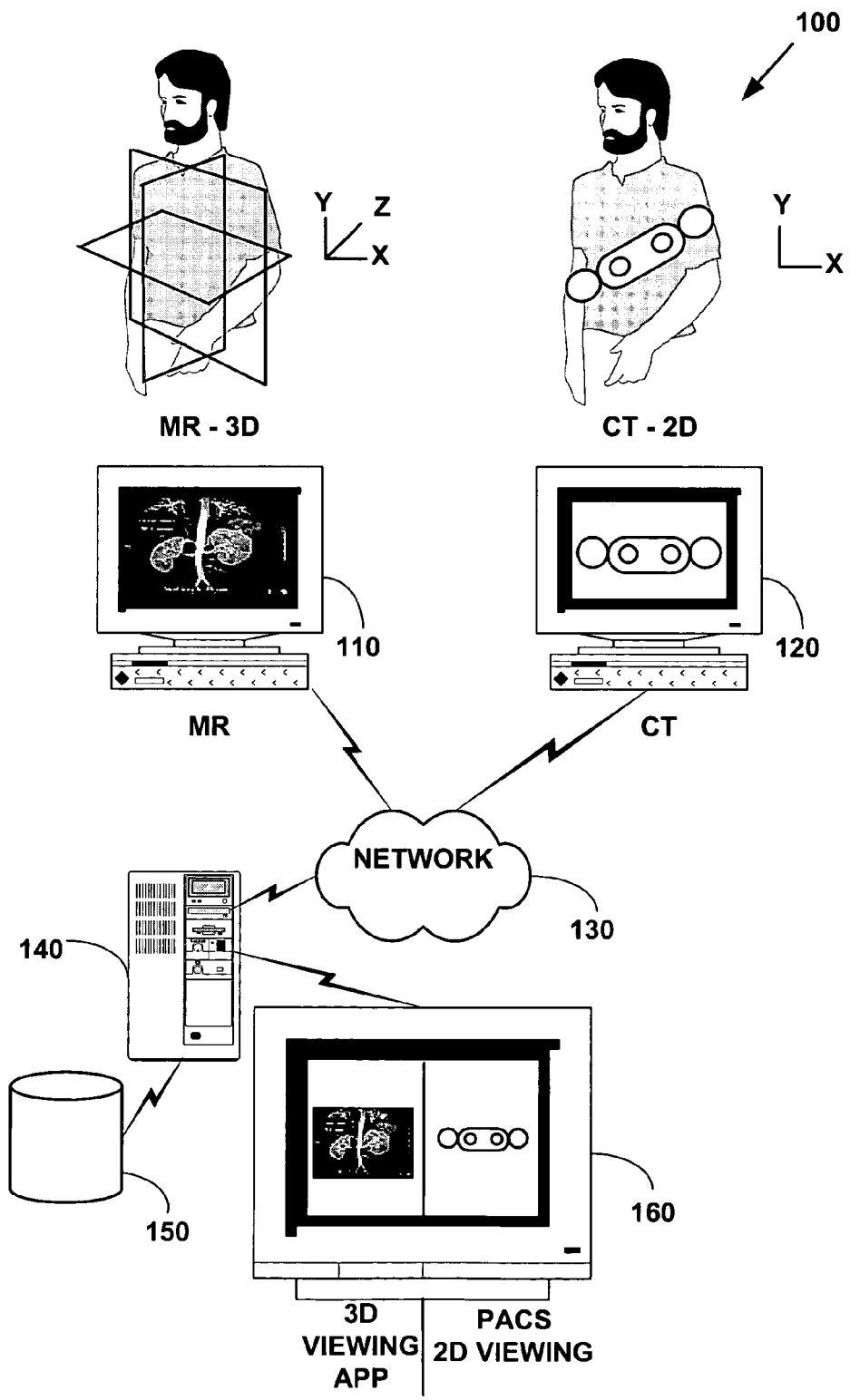
FIG. 1 is a block diagram illustrating an exemplary medical diagnostic image system.

FIG. 1 is a block diagram illustrating an exemplary medical diagnostic image system 100. The medical diagnostic image system 100 includes, but is not limited to, an 3D medical image system 110 (e.g., MR, etc.), a 2D medical image system 120 (e.g., CT, etc.) a communications network 130, one or more server computers 140, one more databases 150 and one or more display devices includes graphical viewing terminals 160. However, more or fewer components can also be used in the medical diagnostic image system 100 and the invention is not limited to these components. The medical diagnostic image system 100 may comprise a portion of a PACS system.

An operating environment for components of the medical diagnostic image system 100 include a processing system with one or more high speed Central Processing Unit(s) ("CPU"), processors and one or more memories. In accordance with the practices of persons skilled in the art of computer programming, the invention is described below with reference to acts and symbolic representations of operations or instructions that are performed by the processing system, unless indicated otherwise. Such acts and operations or instructions are referred to as being "computer-executed," "CPU-executed," or "processor-executed."

It will be appreciated that acts and symbolically represented operations or instructions include the manipulation of electrical signals by the CPU or processor. An electrical system represents data bits which cause a resulting transformation or reduction of the electrical signals and the maintenance of data bits at memory locations in a memory system to thereby reconfigure or otherwise alter the CPU's or processor's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM"), flash memory, etc.) mass storage system readable by the CPU. The computer readable medium includes cooperating or interconnected computer readable medium, which exist exclusively on the processing system or can be distributed among multiple interconnected processing systems that may be local or remote to the processing system.

In one embodiment of the invention, 3D position information is integrated between 2D and 3D viewing paradigms by providing a mechanism called "medical image." However, the 3D cursor name is a moniker only and other moniker can also be used to identify features of the invention. The 3D cursor mechanism provides communication between the 2D and 3D viewing paradigm systems. The 3D cursor mechanism allows for immediate synchronized navigation through different image sets while they are being simultaneously viewed on the two different applications (e.g., the 2D PACS and a 3D visualization application).

Figure 2:
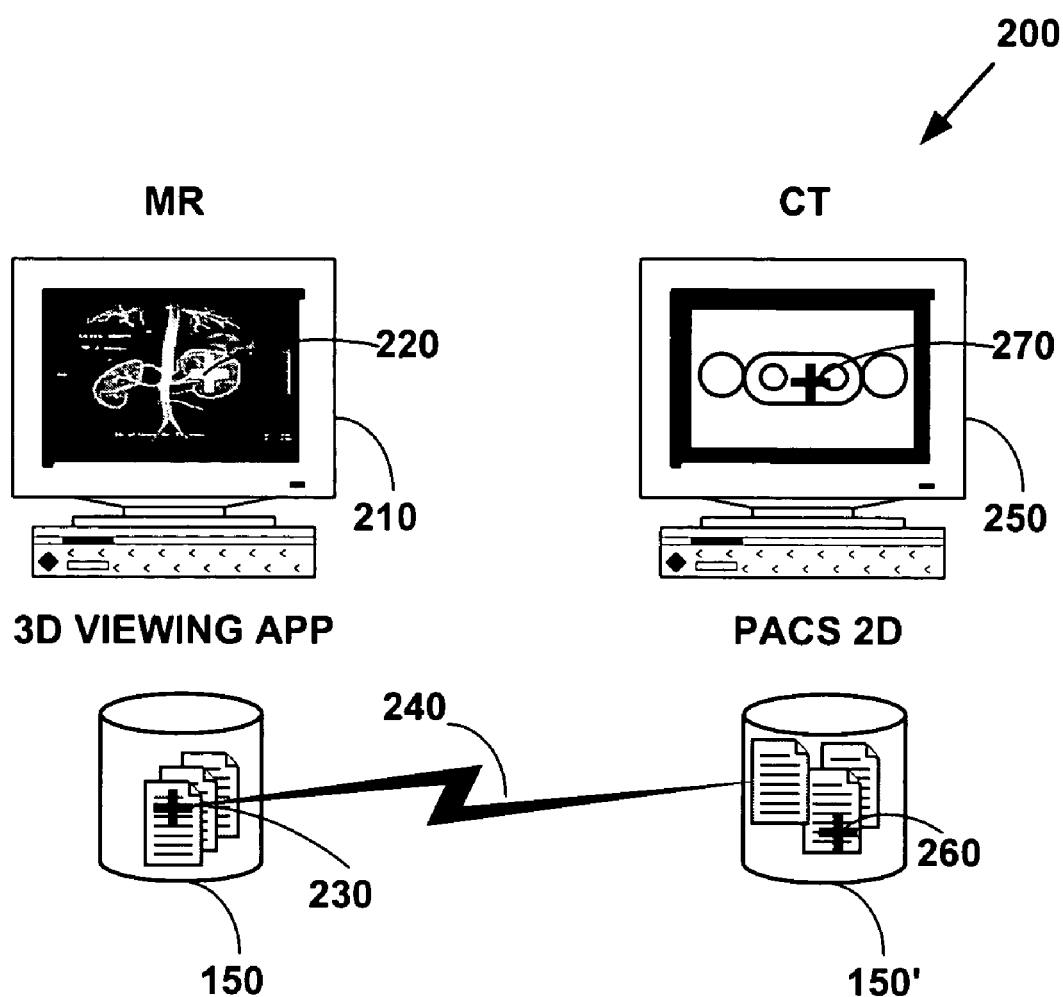
FIG. 2 is a block diagram illustrating exemplary medical image data linking.

FIG. 2 is a block diagram illustrating exemplary medical image linking 200. When a radiologist manipulates a 3D visualization application 210 (e.g., to display sagittal and coronal reformat images) and a point in the 3D space of the patient information is identified via a cross-hair 220 or other mechanism on an image 230, this exact point location will be transmitted 240 to a 2D viewing application such as a PACS system 250 via a standardized format based on the patient coordinate system.

FIG. 2 illustrates the 3D 210 and 2D 250 viewing applications on separate graphical terminals. However, the invention is not limited to such an embodiment. However, these viewing applications may appear on the same display device (i.e., graphical terminal 160) in separate portions of the viewing screen (e.g., separate windows).

In computed tomography, when data from a series of contiguous transverse scan images are made along an axis of a plane or "axial" plane are recombined to produce images in a different plane, such as a sagittal or coronal plane, the images are called "reformat" images. A "sagittal plane" is a median plane of a body dividing the body into left and right halves. A "coronal plane" is a vertical plane through a body from head to foot and parallel to the shoulders, dividing the body into front and back halves.

When the PACS system 250 receives this 3D point via the 3D cursor method it will identify the appropriate image 260 within the base set that contains the point, automatically navigate to that slice, and identify that same point with a marker 270 (cross-hair, etc.). This will occur virtually immediately during simultaneous display of the study within the two viewing applications (210, 250).

The 3D position, or "cursor" is thus linked bidirectionally across the two viewing applications 210, 250, facilitating the correlation of views between them. Similarly, when the radiologist navigates through the base 2D images 260 on the PACS system 250, appropriate 3D cursor information will be transmitted 240 to the 3D visualization application 210 and the appropriate 3D image 230 at the point marker 220.

Exemplary Location Information Linking Architecture

One exemplary architecture for the 3D cursor includes a mechanism for communicating a location of a 3D cursor within a given Digital Imaging and Communications in Medicine (DICOM) series amongst arbitrary software components. However, the present invention is not limited to this embodiment and other embodiments can also be used to practice the invention.

The DICOM standard specifies a hardware independent network protocol utilizing Transmission Control Protocol (TCP) over Internet Protocol (IP) and defines operation of Service Classes beyond the simple transfer of data. It also creates a mechanism for uniquely identifying Information Objects as they are acted upon across a network. DICOM defines Information Objects not only for images but also for patients, studies, reports, and other data groupings. The National Electrical Manufacturers Association (NEMA) DICOM PS 3-2003 standard is incorporated herein by reference.

When the 3D cursor position is directly modified in one of these arbitrary software components, all other components immediately update their views to indicate the new cursor position. 3D cursor synchronization is bidirectional so that a user is free to switch between components, modifying a cursor position from any of them, and having the respective passive components automatically reflect the change in state. No component shall have exclusive "mastership" of the cursor. Any number of software components can participate in 3D cursor sharing. 3D Cursor change events are broadcast to all but the originator of the event.

Figure 3:
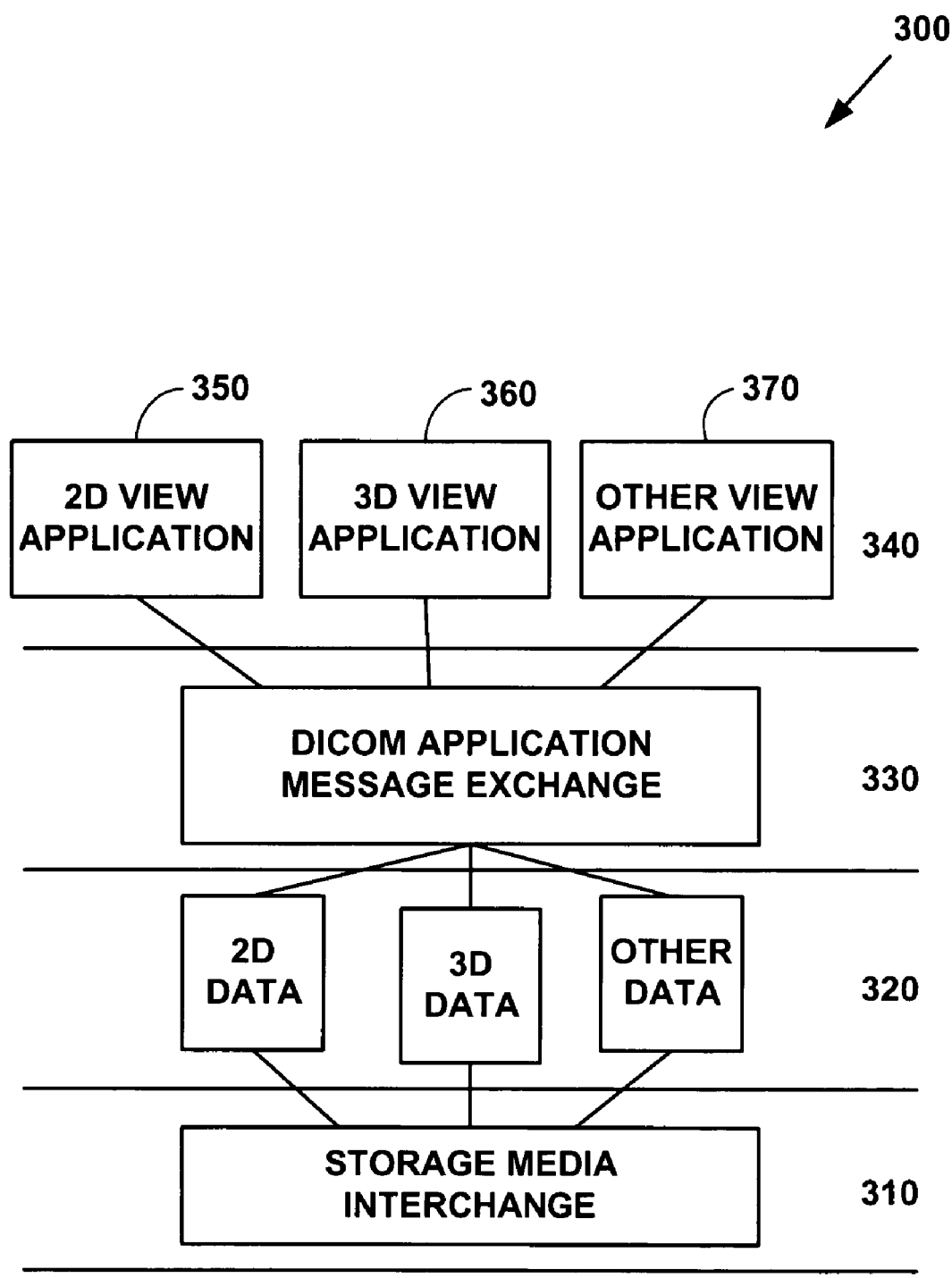
FIG. 3 is a block diagram illustrating an exemplary medical image data linking architecture.

FIG. 3 is a block diagram illustrating an exemplary medical image data linking architecture 300. The medical image data linking architecture includes, but is not limited to, a storage media layer interchange layer 310, a storage media layer 320 including 2D data, 3D data, and other types of data (e.g., text, etc.), a DICOM message exchange layer 330, and a viewing application layer 340 including a 2D viewing application 350 (e.g., PACS), a 3D viewing application 360 and other types of viewing applications 370 (e.g., text, etc.). However, the present invention is not limited to this embodiment and other embodiments can also be used to practice the invention.

Figure 4:
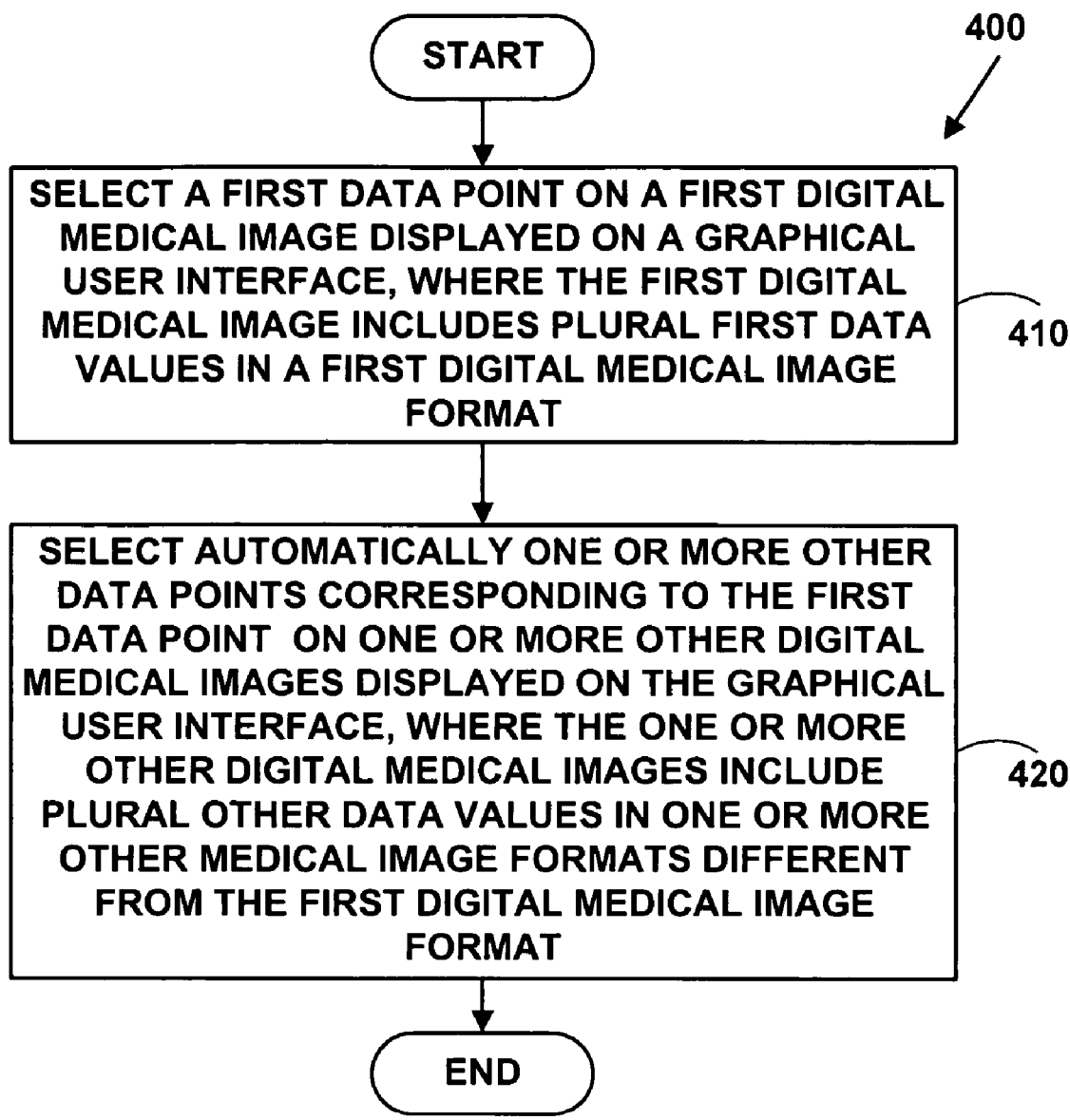
FIG. 4 is a flow diagram illustrating a method for linking points on different medical images.

FIG. 4 is a flow diagram illustrating a Method 400 for linking points on different medical images. At Step 410, a first data point on a first medical image is selected on a display device. The first digital medical image includes plural first data values in a first digital medical image format. At Step 420, one or more other data points corresponding to the first data point are automatically selected on one more other digital medical images displayed on the display device. The one or more other digital medical images include plural other data values in one or more other digital medical image formats different from the first digital medical image format.

Method 400 provides bidirectionally across the two viewing applications facilitating the correlation of views between them. In one embodiment of the invention, the first data point is a 3D data point 220 on an MR image and the one or more other data points are 2D data points 270 on a CT image. In another embodiment of the invention, the first data point is a 2D data point 270 on a CT image and the one or more other data points are one or more 3D data points 220 on an MR image.

In one embodiment of the invention, Method 400 is executed on a PACS system. In another embodiment of the invention, Method 400 is executed on a DICOM system. However, the present invention is not limited to these embodiments and other embodiments can also be used to practice the invention.

One embodiment of the invention includes a medical imaging system with a position information module for providing position information for two different medical viewing formats simultaneously to two different medical viewing applications and a bidirectional communications module for providing bi-direction communications of position information from the position information module between the two different medical viewing applications, thereby allowing for immediate synchronized navigation through different medical image sets from the two different medical viewing formats while they are being simultaneously viewed on the two different medical viewing applications. However, the present invention is not limited to this embodiment and other embodiments can also be used to practice the invention.

Exemplary Location Information Linking Object Architecture

In one exemplary embodiment of the invention, the 3D cursor and Method 400 is implemented using object-oriented objects. However, the invention is not limited to such an embodiment, and other object-oriented and other non-object oriented implementations can also be used.

Figure 5:
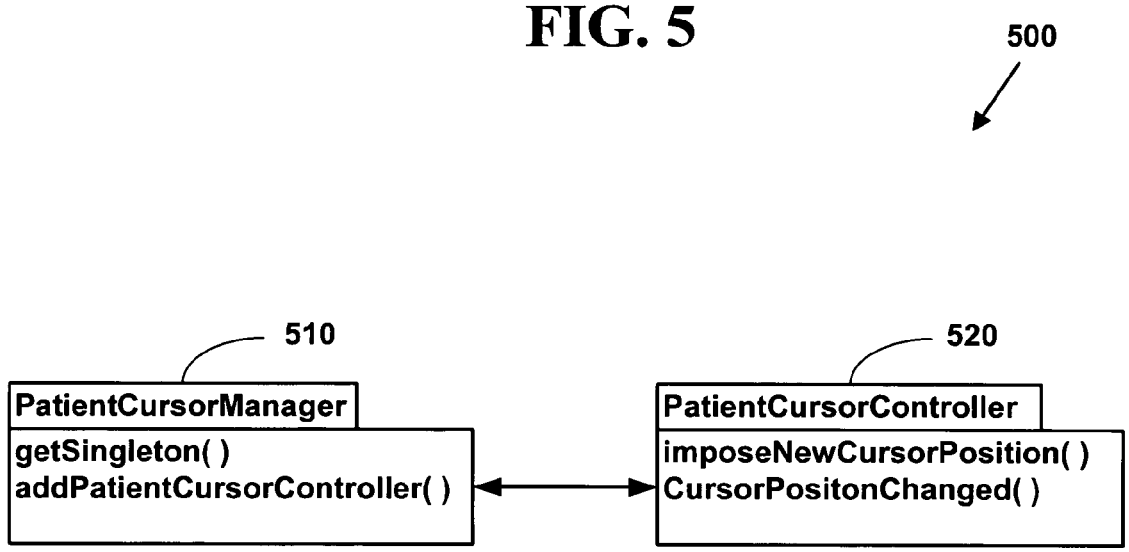
FIG. 5 is a block diagram illustrating an exemplary medical image object architecture.

FIG. 5 is a block diagram illustrating an exemplary medical image object architecture 500.

FIG. 6 is a data flow diagram 600 illustrating details of the medical image object architecture 500 of FIG. 5.

In one embodiment of the invention, the 3D cursor communication is based on communication between two object-oriented objects called "PatientCursorManager( )" 510 and "PatientCursorController( )" 520 However, the invention is not limited to such an embodiment and the 3D cursor communication can be based on other object-oriented objects, or other non-object-oriented objects.

In one embodiment of the invention, the 3D cursor communication is used in a PACS system. In another embodiment of the invention, 3D cursor communication is used on a DICOM system. However, the present invention is not limited to these embodiments and other embodiments can also be used to practice the invention.

These objects interact in a Mediator pattern with PatientCursorManager( ) 510 acting as the Mediator to PatientCursorController( ) 520, which are Colleagues in the Mediator Pattern. Clients add PatientCursorControllers( ) 520 to the singleton PatientCursorManager( ) 510. The PatientCursorManager( ) 510 mediates the 3D cursor position changes amongst all PatientCursorControllers( ) 520.

In one embodiment of the invention, there is no direct interaction amongst the PatientCursorControllers( ) 520. In another embodiment of the invention, there is direct interaction amongst the PatientCursorControllers( ) 520.

The PatientCursorController( ) 520 is modeled as a Singleton pattern. PatientCursorController( )520 is an object base class that provides an interface for components that wish to participate in 3D cursor sharing. In order to participate in 3D cursor sharing, a client component defines a subclass of PatientCursorController( ) 520 and registers an instance of it with the PatientCursorManager( ) 510.

The PatientCursorController( ) 520 implements a "cursorPositionChanged( )" object method to react to changes to the 3D cursor. This in an input method, and is called by the PatientCursorManager( ) 510 to communicate new cursor information when appropriate to each of the PatientCursorControllers( ) 520. When called, the derived PatientCursorController( )520 subclass updates its view to indicate the new 3D cursor location. This update includes moving the 3D cursor on the rendered image, or requires navigation to the correct digital image slice where the indicated location can be found.

Another object method, "imposeNewCursorPosition( )," is provided by the base class implementation of PatientCursorController( ) 520. This method is called whenever any particular PatientCursorController( ) 520 wants to impose a new 3D cursor.

For example, returning to FIG. 6, Client-1 (e.g., a 3D MR viewing application) imposes a new 3D cursor position by calling 610 imposeNewCursorPosition( ). The corresponding PatientCursorController( ) 520 for Client-1 calls 620 controllerChangedCursorPosition( ) in the PatientCursorManger( ) 510. The PatientCursorManager( ) 510 calls 630 cursorPositionChanged( ) in the PatientCursorController( ) 520' for Client-N (e.g., 2D CT PACS viewing application). PatientCursorController( ) 520' for Client-N calls 640 a Client-N specific cursor update method to update a cursor position provided by the 3D cursor information.

In cases where the 3D cursor needs to be synchronized with another application or remote application, the "client" code takes the form of an object adapter that communicates with the external code. This communication based on the communication scheme used by the selected application. For example, the communication includes Component Object Model (COM), Common Object Request Broker Architecture (CORBA), Window's messaging, or other types of communication.

For example, suppose there is an external application called "AW". A CORBA remote method interface is defined for passing 3D cursor information (e.g., "sendPoint"). Within the Centricity application, the adapter class for the AW client application (e.g., 3D MR viewer) creates a PatientCursorController( ) 520 that would field any "sendPoint" calls generated by AW, and relay these to all other PatientCursorControllers( ) 520 via the PatientCursorManager( ) 510 by calling "imposeNewCursorPosition( )". Likewise, this AW adapter PatientCursorController 520 would implement its "cursorPositionChanged( )" method by calling "sendPoint" on the remote AW object.

Note that the above example is only one of many plural possible implementations of the invention. However, the invention is not limited to such an implementation and other implementations can also be used.

Each component and adapter is free to use entirely separate and different mechanisms for the low-level communication. Building on the above example, say another external component "TR" required 3D cursor synchronization, but the only way to communicate this info was via simple "sockets" packets. An adapter and PatientCursorController 520( ) are built for this mechanism.

Although the 3D cursor object architecture 500 is unaware of these separate mechanisms, the loose coupling provides a mechanism whereby the 3D cursor information received from AW via the CORBA "sendPoint" method is automatically translated into the appropriate socket data packet and sent to TR. AW and TR can both participate in the 3D cursor synchronization, whether or not Centricity itself is doing so.

Exemplary Location Information Linking Data Interfaces

In one embodiment of the invention, 3D cursor position data is communicated via arguments in the imposeNewCursorPosition( ) and cursorPositionChanged( ) objects methods. However, the invention is not limited to this embodiment and other object-oriented and non-object oriented embodiments can also be used to communicate 3D cursor data.

Table 1 illustrates exemplary Java object method interfaces that define exemplary 3D cursor position data interfaces used in the 3D cursor object architecture 500. However, the invention is not limited to these Java object method interfaces and other types of interfaces can also be used (i.e., other object-oriented and non-objected-oriented interfaces).

TABLE 1 public final void imposeNewCursorPosition(String seriesInstanceUID, Point3d threeDPoint);
public void cursorPositionChanged(String seriesInstanceUID, Point3d threeDPoint);
Copyright © 2003 by GE Medical Systems, Inc. All rights reserved.

The "Point3d threeDPoint" argument is an object class available in the Java3d "vecmathjar" library, the contents of which are incorporated by reference. Point3D threeDPoint encapsulates an ordered triplet (x,y,z) of three double values.

This argument codes the 3D cursor position in the coordinate space defined by the Image Position and ImageOrientation fields found in DICOM 330 image headers. As long as all client components are aware of this point of reference (which is a well-defined DICOM standard) the positions are coherent amongst them.

The argument "String seriesInstanceUID" provides the DICOM series instance UID for the cursor change. It is assumed that the images in a DICOM series define a 3D "voxel" volumetric space. The 3d position is an (x,y,z) position within this voxel space. The series instance UID is therefore used to communicate which volume the 3D cursor change applies. This allows for a separate 3D cursor for every series.

It is common for applications to be able to display more than one image series at a time, so this information is used for matching up the image correct series. Since the 3D cursor object architecture 500 broadcasts 3D cursor changes to controllers 520 (there is no automatic filtering in the event delivery), each PatientCursorController( ) 520 validates the UID when cursorPositionChanged( ) is called.

The 3D cursor object architecture 500 also provides a way to designate that certain PatientCursorControllers( ) 520 are only interested in 3D cursor changes for specific UIDs.

The method and system described herein provides the integration of at least two distinct viewing paradigms (e.g., 2D and 3D) by providing a standardized mechanism for the communication of 3-dimensional position information via 3D Cursor, between them. This allows for immediate synchronized navigation through the digital image sets while simultaneously viewed on the two applications (e.g., PACS and 3D visualization applications).

However, the method and system described herein is not limited to 2D and 3D viewing paradigms and can also be used to link other medical image diagnostic information together (e.g., text, etc.).

It should be understood that the architecture, programs, processes, methods and systems described herein are not related or limited to any particular type of computer or network system (hardware or software), unless indicated otherwise. Various types of general purpose or specialized computer systems may be used with or perform operations in accordance with the teachings described herein.

While various elements of the preferred embodiments have been described as being implemented in software, in other embodiments hardware or firmware implementations may alternatively be used, and vice-versa.

In view of the wide variety of embodiments to which the principles of the invention can be applied, it should be understood that the illustrated embodiments are exemplary only, and should not be taken as limiting the scope of the invention. For example, the steps of the flow diagrams may be taken in sequences other than those described, and more or fewer elements may be used in the block diagrams.

The claims should not be read as limited to the described order or elements unless stated to that effect. In addition, use of the term "means" in any claim is intended to invoke 35 U.S.C. §112,paragraph 6,and any claim without the word "means" is not so intended. Therefore, all embodiments that come within the scope and spirit of the following claims and equivalents thereto are claimed as the invention.

I claim:

1. A method for linking data points on medical images, comprising:
    using a processor to perform the steps of:
        selecting a first data point on a first digital medical image on a display device, wherein the first digital medical image includes a plurality of data points in a first digital medical image format; and
        automatically selecting one or more other data points corresponding to the first data point on one or more other digital medical images displayed on the display device, wherein the one or more other digital medical images include a plurality of other data points in one or more other digital medical image formats different from the first digital medical image format, thereby allowing for immediate synchronized bidirectional navigation between the first digital medical image and the one or more medical images.

2. The method of claim 1 wherein a computer readable medium having stored therein instructions causes a processor to execute the steps of the method.

3. The method of claim 1 wherein the first digital medical image format includes a magnetic resonance image format and the one or more other digital medical image formats include computed tomography image formats.

4. The method of claim 1 wherein the first digital medical image format includes a computed tomography image format and the one or more other digital medical image formats include magnetic resonance image formats.

5. The method of claim 1 wherein the first data point includes a three-dimensional data point and the one or more other data points include two-dimensional data points.

6. The method of claim 1 wherein the first data point includes a two-dimensional data point and the one or more other data points include three-dimensional data points.

7. The method of claim 1 wherein the method is executed on a Picture Archive and Communication System (PACS).

8. The method of claim 1 wherein the method is executed on a Digital Image and Communications in Medicine (DICOM) system.

9. The method of claim 1 wherein the first data point is accessed via a first set of object-oriented objects and the one or more other data points are accessed via a second set of object oriented objects.

10. A medical imaging system, comprising:
a computer-readably medium;
a position information means configured on the computer-readable medium for providing position information for two different medical viewing formats simultaneously to two different medical viewing applications; and
a bidirectional communications means configured on the computer-readable medium for providing bi-direction communications of position information from the position information means between the two different medical viewing applications, thereby allowing for immediate synchronized navigation through different medical image sets from the two different medical viewing formats while they are being simultaneously viewed on the two different medical viewing applications.

11. The medical imaging system of claim 10 wherein the two different viewing formats include a three-dimensional medical viewing format and a two-dimensional medical viewing format.

12. The medical imaging system of claim 11 wherein the three-dimensional medical viewing format includes a magnetic resonance image format.

13. The medical imagines system of claim 11 wherein the two-dimensional medical viewing format includes a computed tomography image format.

14. The medical imaging system of claim 10 wherein the position information means and the bidirectional communications means comprise one or more object-oriented objects.

15. The medical imaging system of claim 10 wherein the medical imaging system is included on a Picture Archive and Communication System (PACS).

16. The medical imaging system of claim 10 wherein the medical imaging system is included on a Digital Image and Communications in Medicine (DICOM) system.

17. A method for linking data points on medical images, comprising:
using a processor to perform the steps of:
selecting a first data point on a first digital medical image on a display device, wherein the first digital medical image includes a plurality of data points in a three-dimensional medical image format; and
automatically selecting one or more other data points corresponding to the first data point on a second digital medical image displayed on the display device, wherein the second digital medical image includes a plurality of second data points in a two-dimensional medical image format, thereby allowing for immediate synchronized bidirectional navigation between the three-dimensional first digital medical image and the two-dimensional second digital medical image.

18. The method of claim 17 wherein a computer readable medium having stored therein instructions causes a processor to execute the steps of the method.

19. The method of claim 17 wherein the three-dimensional medical imaging format includes a magnetic resonance image format.

20. The method of claim 17 wherein the two-dimensional medical imaging format includes a computed tomography image format.

* * * * *